United States Patent [19]

Weinberger

[11] Plant 4,927

[45] Nov. 9, 1982

[54] NECTARINE TREE (83-50)

[75] Inventor: John H. Weinberger, Fresno, Calif.

[73] Assignee: Superior Farming Company, Bakersfield, Calif.

[21] Appl. No.: 271,529

[22] Filed: Jun. 8, 1981

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is of medium size and vigor, upright-spreading, dense, and round-topped; foliated with medium size, ovate, long-lanceolate, acutely pointed leaves having a crenate margin, a petiole medium in length and thickness, and irregularly alternate, medium size, reniform glands positioned on the petiole and base of the blade; flowers from buds which are of medium size and length, plump, appressed, and pubescent; the flowers, of medium season, being large and pink; and is a regular and productive bearer of medium size, uniform, symmetrical, globose, freestone fruit having yellow skin substantially overspread with red, yellow flesh mottled with red next to the stone, and a tan stone.

1 Drawing Figure

BACKGROUND OF THE VARIETY

1. Field of the Invention

In the conduct of an extensive plant breeding program — on behalf of a commercial farming company, and in such company's experimental orchard located near Fresno, Fresno County, Calif. — I have originated a substantial number of new and distinct varieties of fruit trees, and which include the present variety of nectarine tree.

2. Classification of the Variety

The present variety of nectarine tree is embraced by Class 41, Plants, of the U.S. Patent Office Manual of Classification.

3. Prior Varieties

Among existing varieties of nectarine trees which are known to me, and mentioned herein, are the Summer Grand (U.S. Plant Pat. No. 2,879) and the Early Sun Grand (U.S. Plant Pat. No. 1,420).

ORIGIN OF THE VARIETY

The present variety of nectarine tree was originated by me as an open-pollinated seedling of the Summer Grand nectarine tree. A number of such seedlings were grown to fruition, in the aforesaid experimental orchard, under careful and continuing observation by me; the present variety being a selection of one of such open-pollinated seedlings.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of nectarine tree is, characteristically, of medium size and vigor, upright-spreading, dense, and round-topped, foliated with medium size, ovate, long-lanceolate, acutely pointed leaves having a crenate margin, a petiole medium in length and thickness, and irregularly alternate, medium size, reniform glands positioned on the petiole and base of the blade; flowers from buds which are of medium size and length, plump, appressed, and pubescent; the flowers, of medium season, being large and pink; and is a regular and productive bearer of medium size, uniform, symmetrical, globose, freestone fruit having yellow skin substantially overspread with red, yellow flesh mottled with red next to the stone, and a tan stone.

The present variety of nectarine tree is further, and more particularly, characterized by fruit which most nearly resembles the fruit of the Summer Grand in form, color, and appearance, but ripens about three weeks earlier than the Summer Grand.

The present variety of nectarine tree is still further characterized by fruit which, in comparison to the fruit of the Early Sun Grand, ripens about the same time, but differs by a less elongated fruit form, and a rounded apex with only an occasional point as contrasted with the point typical at the apex of the Early Sun Grand. Additionally, the fruit of the present variety is absent the usual enlargement, on one side of the suture and at shipping ripe stage, of the fruit of the Early Sun Grand.

BRIEF DESCRIPTION OF THE DRAWING

The drawing is an illustration, by photographic reproduction in color, of a twig with leaves and separate fruit; one fruit being halved, with the stone remaining in one half.

DESCRIPTION OF THE VARIETY

The botanical details of this new and distinct variety of nectarine tree — with color definitions (except those in common color terms) referenced to Plochere Color System (in book form) — are as follows:

Tree:

*Size.*—Medium.
*Vigor.*—Medium.
*Growth.*—Upright-spreading.
*Density.*—Dense.
*Form.*—Round-topped.
*Production.*—Productive.
*Bearing.*—Regular bearer.

Trunk:

*Size.*—Medium.
*Texture.*—Medium.

Branches:
*Size.*—Medium.
*Texture.*—Medium.
*Color.*—New wood: Green. Dull. Reddish brown on ventral side. Mature wood: Brown.

Leaves:
*Size.*—Medium. Average length — 16.4 cm. Average width — 4.4 cm.
*Form.*—Ovate. Long-lanceolate. Acutely pointed.
*Thickness.*—Medium.
*Color.*—Medium green.
*Texture.*—Smooth.
*Margin.*—Crenate.
*Petiole.*—Medium length. Medium thickness.
*Glands.*—Average number — 3. Alternate — irregular. Medium size. Reniform. Green. Positioned distal on petiole and basal on blade.
*Stipules.*—Shed with leaf maturity.

Flower buds:
*Size.*—Medium.
*Length.*—Medium.
*Form.*—Plump. Appressed. Pubescent.

Flowers:
*Date of full bloom.*—Mar. 9th, 1980. Medium, as compared with other varieties.
*Size.*—Large.
*Color.*—Pink.

Fruit:
*Maturity when described.*—Firm ripe — June 27th, 1980.
*Date of first picking.*—June 23rd, 1980.
*Date of last picking.*—July 1st, 1980.
*Size.*—Medium. Average diameter axially — 64 mm. Average transversely in suture plane — 63 mm.
*Form.*—Uniform. Symmetrical. Globose.
*Suture.*—A shallow, inconspicuous line extending from base to beyond apex, with slight depression beyond pistil point.
*Ventral surface.*—Rounded. Lipped throughout.
*Lips.*—Equal.
*Cavity.*—Rounded. Elongated in suture plane, with suture showing on one side. Average depth — 10 mm. Average breadth — 17 mm.
*Markings.*—None.
*Base.*—Rounded.
*Apex.*—Depressed.
*Pistil point.*—Apical.

Skin:
*Thickness.*—Medium.
*Texture.*—Medium.
*Tenacity.*—Tenacious to flesh.

*Tendency to crack.*—None in dry season.
*Color.*—Ground color — Yellow. Blush color — Red (Plate 11 — No. 241 — Scarlet).
*Down.*—Wanting.

Flesh:
*Color.*—Yellow (Plate 7 — No. 147 — Nasturtium) mottled with red next to stone.
*Amygdalin.*—Wanting.
*Juice.*—Moderate.
*Texture.*—Medium. Fine. Melting.
*Fibers.*—Few. Fine.
*Ripens.*—Evenly.
*Flavor.*—Acid. Delicate.
*Aroma.*—Distinct.
*Eating quality.*—Best.

Stone:
*Type.*—Free.
*Fibers.*—Short. Retains short fiber-like threads along edges.
*Size.*—Medium. Average length — 35 mm. Average breadth — 25 mm. Average thickness — 20 mm.
*Form.*—Elliptical. Cuneate toward base.
*Base.*—Straight.
*Hilum.*—Narrow — oval.
*Apex.*—Acuminate.
*Sides.*—Equal.
*Surface.*—Regularly furrowed near ventral edge and toward apex. Ridged toward apex. Pitted toward base above center.
*Ridges.*—Rounded toward apex. Continuous.
*Pits.*—Elongated.
*Ventral edge.*—Thick, without wing throughout.
*Dorsal edge.*—Full. Shallow throughout.
*Color.*—Tan (Plate 9 — No. 213 — Apricot Tan).
*Tendency to split.*—Slight in dry season.

Use: Market.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, characterized by freestone fruit in harvest about three weeks earlier than the fruit of the Summer Grand and about with the fruit of the Early Sun Grand.

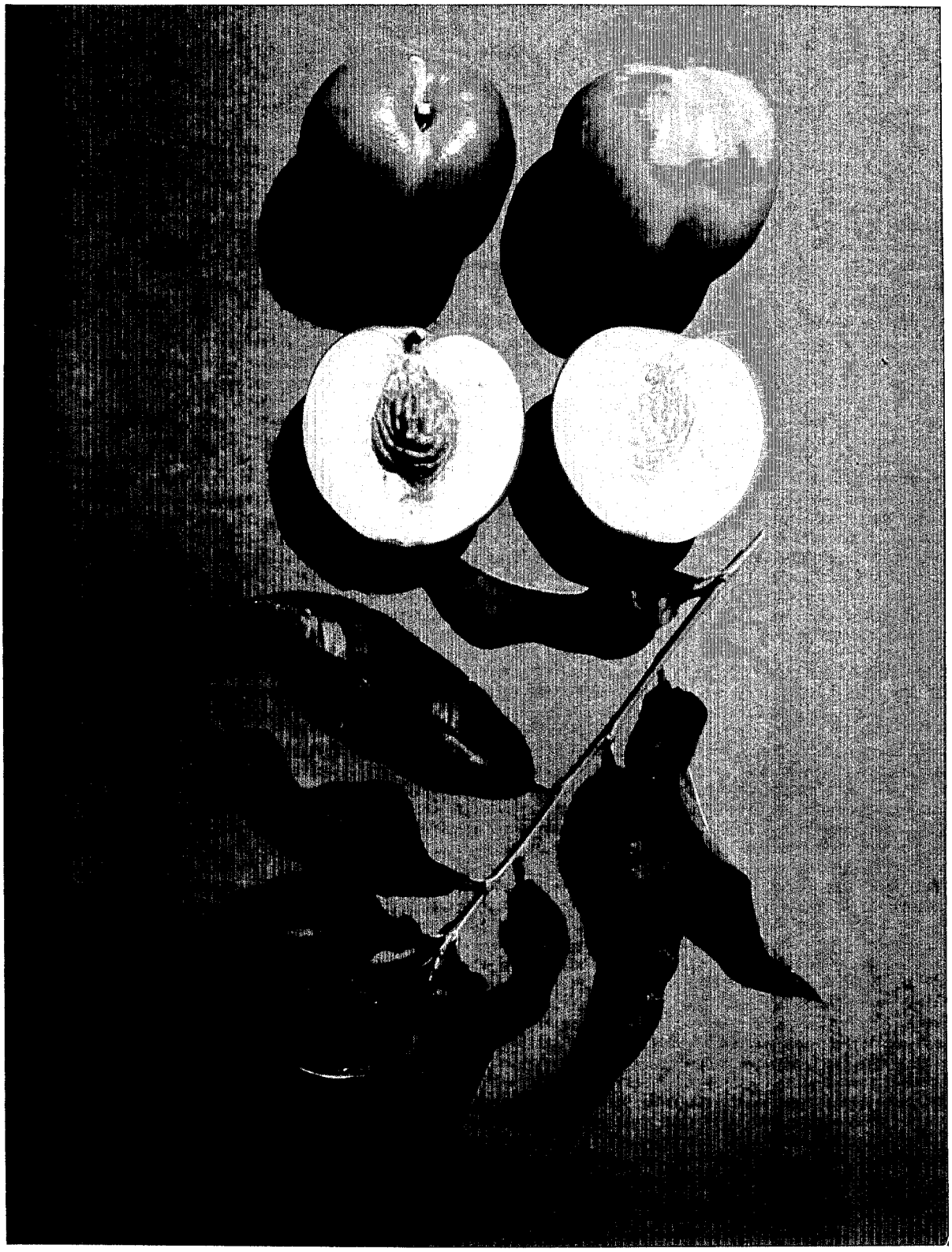

* * * * *